United States Patent
Shen et al.

(10) Patent No.: US 7,437,947 B1
(45) Date of Patent: Oct. 21, 2008

(54) ACOUSTIC METHOD FOR MEASURING FLOW VELOCITY OF FLUID

(75) Inventors: Che-Chou Shen, Taipei County (TW); Ching-Han Chou, Taipei County (TW)

(73) Assignee: National Taiwan University of Science and Technology, Taipei (TW)

( * ) Notice: Subject to any disclaimer, the term of this patent is extended or adjusted under 35 U.S.C. 154(b) by 0 days.

(21) Appl. No.: 11/782,885

(22) Filed: Jul. 25, 2007

(30) Foreign Application Priority Data

Jun. 11, 2007 (TW) .............................. 96120961 A (51) Int. Cl.
*G01F 1/66* (2006.01)
(52) U.S. Cl. .................................................. 73/861.25
(58) Field of Classification Search .............. 73/861.25; 600/454, 455
See application file for complete search history.

(56) References Cited

U.S. PATENT DOCUMENTS 5,928,153 A * 7/1999 Chiang et al. ............... 600/454
6,142,944 A * 11/2000 Li et al. ...................... 600/453

* cited by examiner

*Primary Examiner*—Jewel Thompson
(74) *Attorney, Agent, or Firm*—J.C. Patents (57) ABSTRACT

An acoustic method for measuring flow velocity of fluid is provided. First, a sound wave is emitted from a transduction surface of a transducer to a fluid. The transduction surface has at least two signal transduction sections. When the sound wave is scattered into a scattered signal by the fluid, the scattered signal is received by the transduction sections. According to the scattered signal, the maximum Doppler frequencies are calculated. Then, according to these maximum Doppler frequencies, the flow velocity of fluid is calculated.

8 Claims, 6 Drawing Sheets

ACOUSTIC METHOD FOR MEASURING FLOW VELOCITY OF FLUID

CROSS-REFERENCE TO RELATED APPLICATION

This application claims the priority benefit of Taiwan application serial no. 96120961, filed on Jun. 11, 2007. All disclosure of the Taiwan application is incorporated herein by reference.

BACKGROUND OF THE INVENTION

1. Field of the Invention

The present invention relates to a method for measuring flow velocity of fluid, and more specifically, relates to an acoustic method for measuring flow velocity of fluid.

2. Description of Related Art

In current medical projects, ultrasound is applied to monitor organs and blood vessels in human body, and the Doppler Effect of ultrasound may be applied to measure the blood flow velocity of a portion of a certain blood vessel, which serves as important information to diagnose blood vessel choke and aneurysm.

Figure 1A:
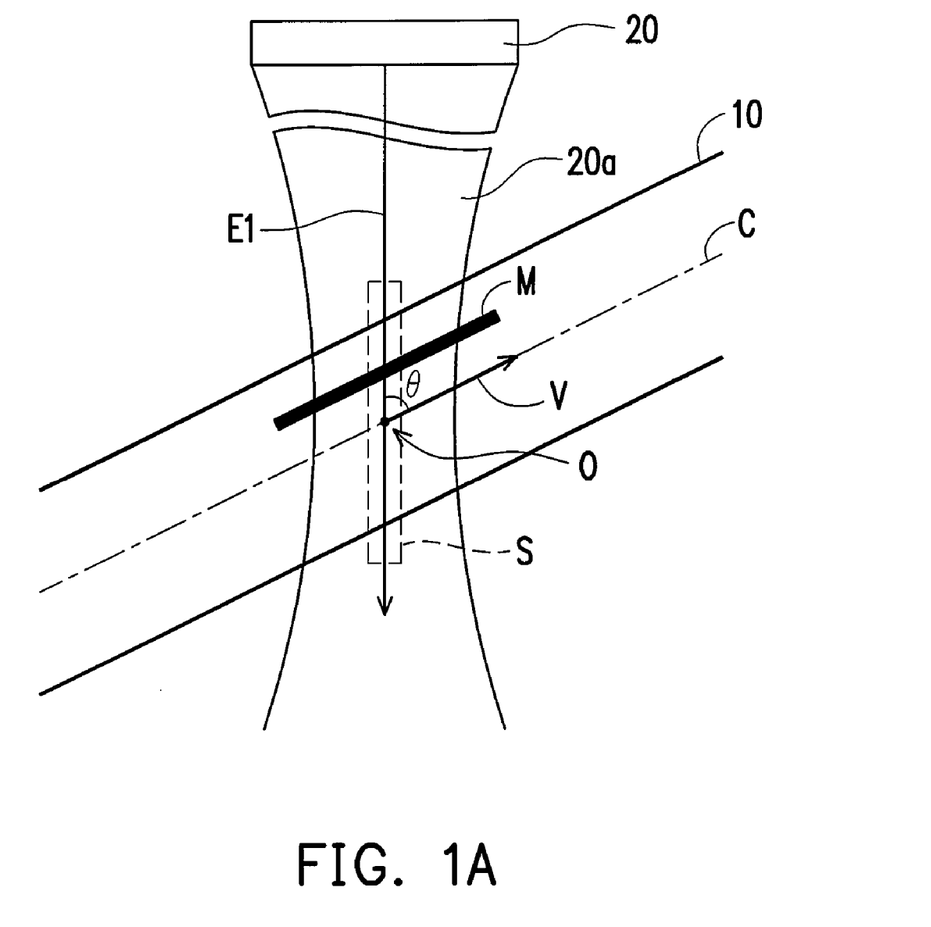
FIG. 1A is a schematic diagram of a conventional method for measuring blood flow velocity in blood vessel.

FIG. 1A is a schematic diagram of a conventional method for measuring blood flow velocity in blood vessel. Referring to FIG. 1A, when blood vessel 10 is imaged using ultrasound, a sample volume S may be designated on a certain portion of blood vessel 10. Next, an ultrasonic beam 20a emitted by an ultrasonic transducer 20 may travel along the advancing direction E1, and travel through the sample volume S. The acoustic beam 20a may be scattered by the blood in blood vessel 10 and becomes ultrasound echo signal when passing through the sample volume S (not shown in FIG. 1A). After receiving the ultrasound echo signal, the ultrasonic transducer 20 analyses the frequency of the ultrasound echo signal to obtain the Doppler shift frequency, and the blood flow velocity V is calculated.

According to the above description, the conventional method for calculating the blood flow velocity V may be calculated by the following equation. Doppler shift frequency, and the equation of Doppler shift frequency is shown as the equation (1) below:

$$f_d = \frac{2V\cos\theta}{\lambda} \quad (1)$$

In equation (1), $f_d$ is Doppler shift frequency, Doppler shift frequency, $\lambda$ is the wavelength of ultrasonic beam 20a, and $\theta$ is Doppler angle which is the angle between the traveling direction E1 of the acoustic beam 20a and the direction of the blood flow velocity V. $f_d$ can be acquired via measurement, and $\lambda$ is a given parameter.

The method of measuring the Doppler angle $\theta$ includes observing the blood vessel 10 image formed by ultrasound with naked eyes and manually marking a direction marker M in the sample volume S. The direction marker M is parallel to the blood vessel 10 shown in FIG. 1A. That is, the direction marker M represents the direction of the blood flow velocity V, and the Doppler angle $\theta$ is obtained.

However, the Doppler angle $\theta$ measured by the above method may be affected by manual observation and result in relatively bigger error. Secondly, the blood vessel 10 shown in FIG. 1A is a real blood vessel 10's two-dimensional image projected on screen. Therefore, actually the direction marker M might not parallel to the real blood vessel 10. Therefore, the Doppler angle $\theta$ measured using the direction marker M is prone to miscalculation on the blood flow velocity V. To address the above shortcomings, nowadays it is proposed to use Doppler bandwidth in Doppler spectrum to calculate the lateral component of the blood flow velocity V (i.e. V sin $\theta$) to obtain the blood flow velocity V.

Figure 1B:
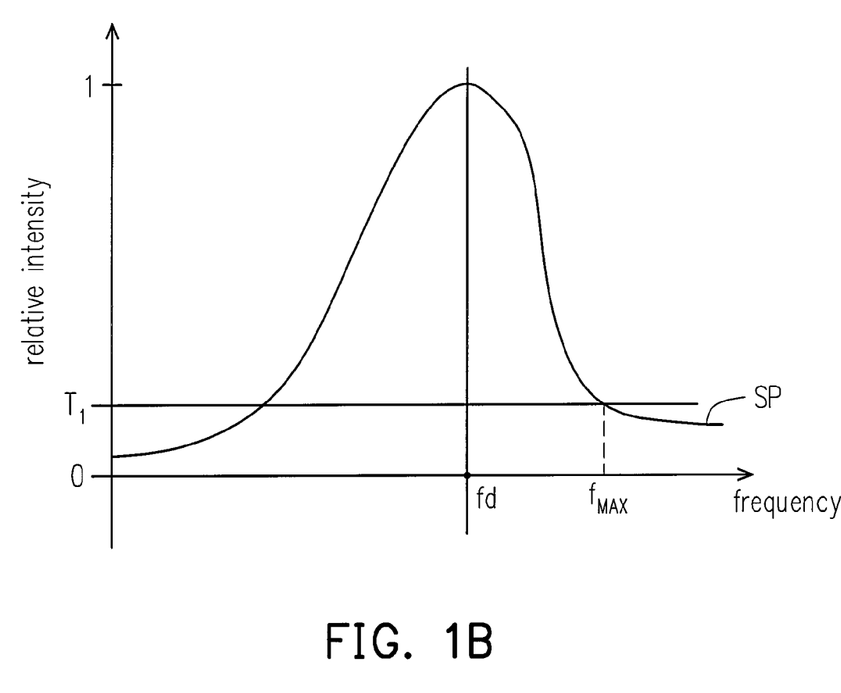
FIG. 1B is a Doppler spectrum graph based on ultrasound echo signal measured in the sample volume in FIG. 1A.

FIG. 1B is a Doppler spectrum graph based on ultrasound echo signal measured in the sample volume in FIG. 1A, wherein the vertical axis denotes the relative intensity of ultrasound echo signal, while the horizontal axis denotes the frequency. Referring to FIG. 1A and FIG. 1B, the Doppler spectrum SP is drawn through subjecting the ultrasound echo signal in the sample volume S to Fast Fourier Transformation (FFT). The frequency that the largest intensity value of the Doppler spectrum SP corresponds to is Doppler shift frequency $f_d$, i.e. the Doppler shift frequency that is generated by the axis component V cos $\theta$ of the blood flow velocity V. When the relative intensity is a predetermined threshold T1, the frequency of the corresponding predetermined threshold T1 is the maximum Doppler frequency $f_{max}$. The Doppler bandwidth in FIG. 1B satisfies the following equations (2) and (3):

$$B_d = 2|f_{max} - f_d| \quad (2)$$

$$B_d = \frac{2W \cdot V\sin\theta}{\lambda F} \quad (3)$$

Wherein, $B_d$ is Doppler bandwidth. In equation (3), W is the diameter of emitting source of the ultrasonic transducer 20, while F is the focal depth of the ultrasound acoustic beam 20a. W and F are given parameters, and the maximum Doppler bandwidth $f_{max}$ and Doppler shift bandwidth $f_d$ can be obtained from FIG. 1B, therefore the lateral component V sin $\theta$ of the blood flow velocity V can be calculated from the equation (2) and (3), and the blood flow velocity V can be obtained.

However, the Doppler shift bandwidth $f_d$ in FIG. 1B may vary with the location of the sample volume S. More specifically, if the center O of the sample volume S deviates from the axis C of blood vessel 10, then the Doppler shift bandwidth $f_d$ may change, which results in error in calculation of the blood flow velocity V.

SUMMARY OF THE INVENTION

The present invention provides an acoustic method for measuring the flow velocity of fluid, which can calculate the flow velocity of fluid more accurately.

The present invention provides an acoustic method for measuring flow velocity of fluid comprises the following steps. First, a sound wave is transmitted from a transduction surface of a transducer to a fluid, wherein the transduction surface has at least two signal transduction sections Dn, and n is a positive integer representing the number of the signal transduction sections. Next, when the sound wave is scattered by the fluid and becomes a scattered signal, the scattered signal is received from these transduction sections Dn. According to the scattered signal received by these transduction sections Dn, a plurality of maximum Doppler frequencies fn are calculated. Next, the flow velocity of the fluid is calculated based on these maximum Doppler frequencies fn.

The present invention uses at least two maximum Doppler frequencies to measure the flow velocity of fluid. Compared to the prior arts, the present invention can measure the flow velocity of fluid without knowing the Doppler shift frequency. Therefore the present invention can obtain the flow velocity of fluid accurately without being affected by the shift of Doppler shift frequency.

In order to the make the aforementioned and other objects, features and advantages of the present invention comprehensible, a preferred embodiment accompanied with figures is described in detail below.

DESCRIPTION OF EMBODIMENTS

Figure 2A:
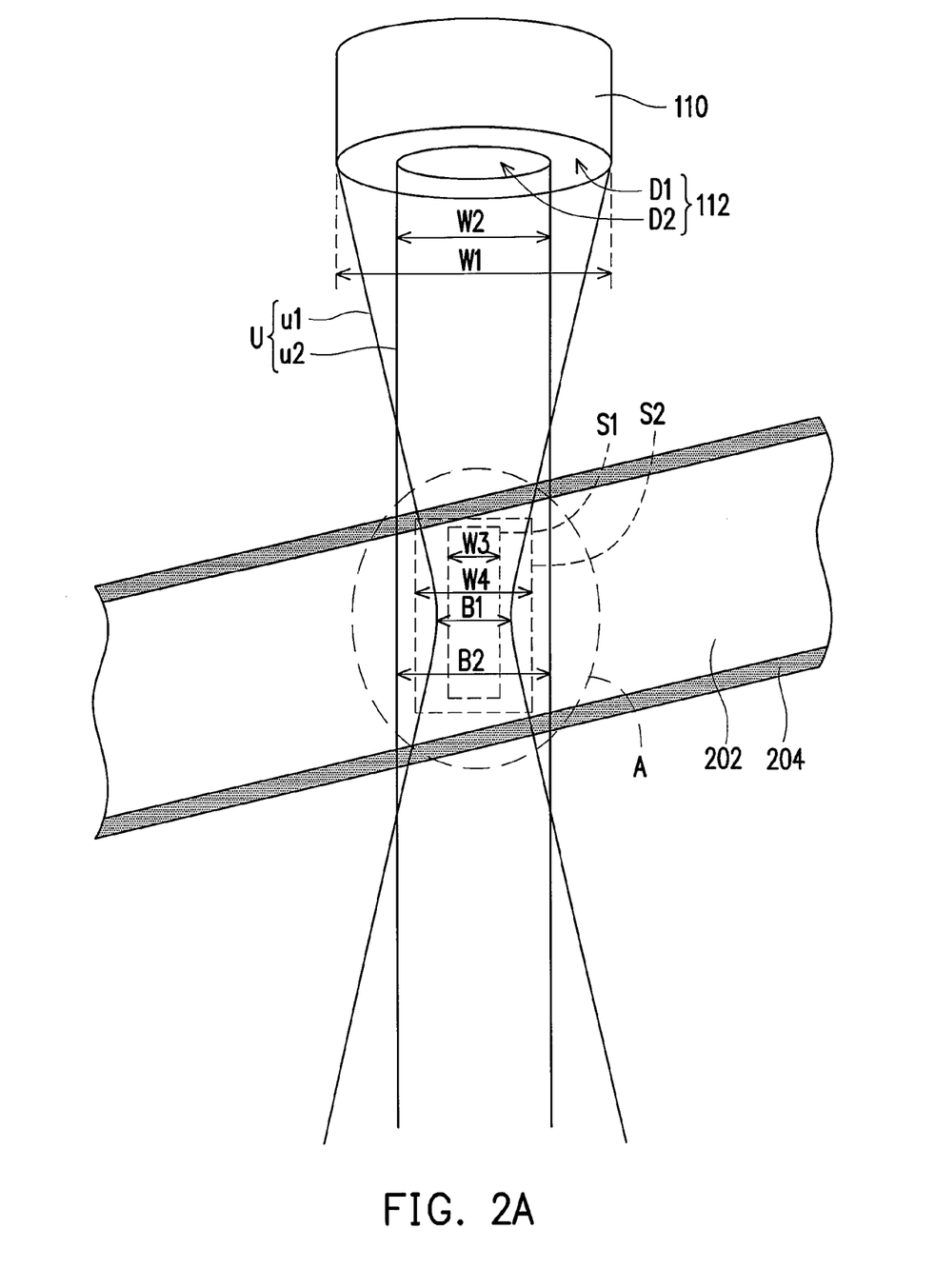
FIG. 2A is a schematic diagram of an acoustic method for measuring flow velocity of fluid according to an embodiment of the present invention.
Figure 2B:
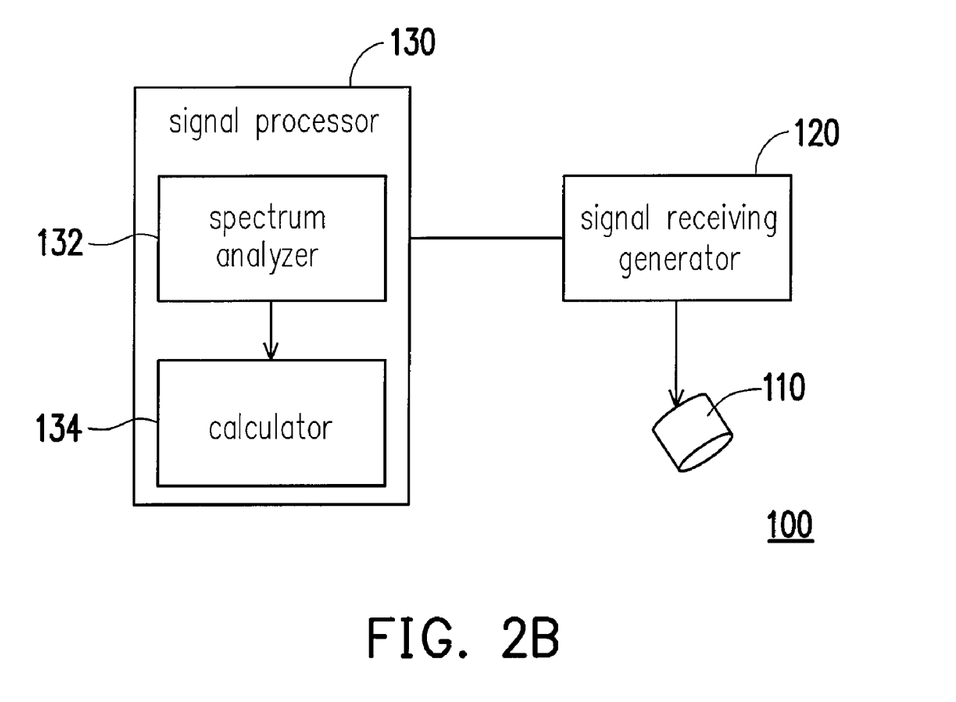
FIG. 2B is a block diagram of an applicable measuring system for an embodiment of the present invention.

FIG. 2A is a schematic diagram of an acoustic method for measuring flow velocity of fluid according to an embodiment of the present invention, and FIG. 2B is a block diagram of an applicable measuring system for an embodiment of the present invention. Referring to FIG. 2A and FIG. 2B, the measuring system 100 includes a transducer 110, a signal receiving generator 120 and a signal processor 130. The transducer 110 is electrically connected to the signal receiving generator 120 and the signal receiving generator 120 is electrically connected to the signal processor 130. The signal receiving generator 120 can control the transducer 110 to emit sound wave U and to receive the scattered signal (not shown) which is sound wave U scattered by fluid 202. The scattered signal is a sound signal. When the transducer 110 receives the scattered signal, the scattered signal may be transformed into electric signal, and the signal receiving generator 120 transmits the electric signal to the signal processor 130, so that the signal processor 130 processes the electric signal.

The acoustic method for measuring flow velocity of fluid of the present embodiment includes the following steps. First, sound wave U is transmitted to fluid 202 from a transduction surface 112 of the transducer 110, fluid 202, for example, flows in a tube 204. Fluid 202 has the characteristic of scattering sound, wherein the fluid 202 may be blood, water bubble or other fluid that can scatter sound. The transduction surface 112 has at least two signal transduction sections D1 and D2, and sound wave U is emitted from the signal transduction sections D1, D2 through vibrating the transduction surface 112. In addition, sound wave U may be a focused acoustic beam, and the tube 204 may pass through the focal point A of sound wave U, as shown in FIG. 2A.

In the present embodiment, the area of the signal transduction section D2 may be smaller than the area of the signal transduction section D1, and the signal transduction section D2 is located inside the signal transduction section D1. That is, the range of the signal transduction section D1 covers the whole signal transduction section D2, and the signal transduction section D1 and the signal transduction section D2 overlaps with each other, and the width W2 of the signal transduction section D2 is smaller than the width W1 of the signal transduction section D1.

Figure 2C:
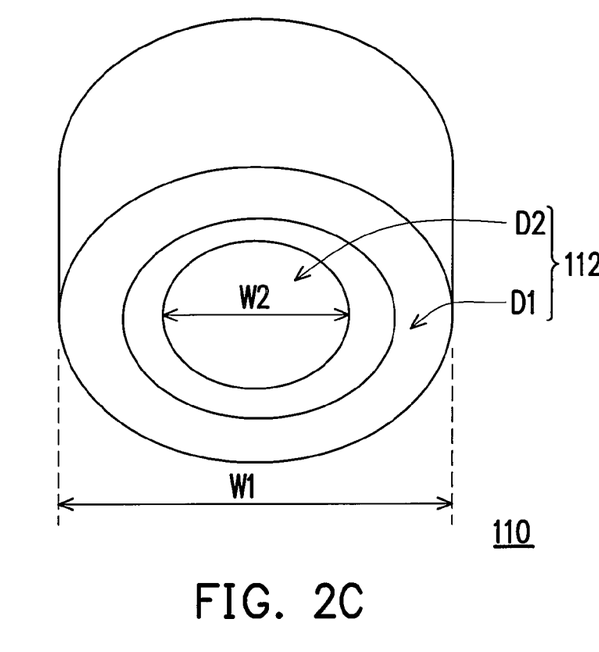
FIG. 2C is a 3-D view of the transducer in FIG. 2A.
Figure 2D:
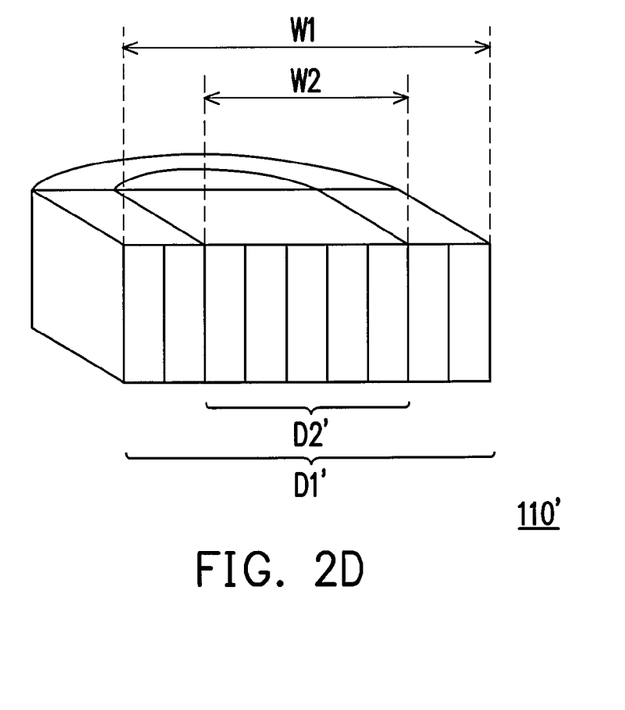
FIG. 2D is a 3-D view of another transducer according to an embodiment of the present invention.

The transducer 110 may be an annular array transducer, and the shapes of the signal transduction section D1 and the signal transduction section D2 thereof, for example, are circular, as shown in FIG. 2C. Therefore, the width W1 is the diameter of the signal transduction section D1, and the width W2 is the diameter of the signal transduction section D2. In addition, the transducer of the present invention may also be a linear array transducer, as the transducer 110' shown in FIG. 2D. Referring to FIG. 2D, the shapes of the signal transduction section D1' and the signal transduction section D2' of the transducer 110', for example, are rectangular, and the width W1 of the signal transduction section D1' is the long side of the signal transduction section D1', and the width W2 of the signal transduction section D2' is the long side of the signal transduction section D2'.

Since the transducer 110 (or 110') has two signal transduction sections D1, D2 (or D1', D2'), therefore the sound wave U includes two acoustic beams U1 and U2 respectively generated by the signal transduction sections D1, D2. Wherein the traveling directions of the acoustic beams U1 and U2 are the same. That is, the acoustic beam U1 and the acoustic beam U2 are pointed to the fluid 204 in tube 204 at the same Doppler angle, i.e. the angles between the traveling directions of the acoustic beams U1, U2 and the tube 204 are the same. The acoustic beam U1 and the acoustic beam U2 overlap each other, and in the focal point A, the width B1 of the acoustic beam U1 is smaller than the width B2 of the acoustic beam U2. Therefore a sample volume S1 can be designated according to the acoustic beam U1, and a sample volume S2 can be designated according to the acoustic beam U2, wherein the sample volume S1 and the sample volume S2 overlap each other, and the width W4 of the sample volume S2 is larger than the width W3 of the sample volume S1, as shown in FIG. 2A.

Again, referring to FIG. 2A and FIG. 2B, when sound wave U passes through fluid 202, fluid 202 may scatter sound wave U into a scattered signal (not shown in FIG. 2A), and the transducer 110 receives the scattered signal from the signal transduction sections D1, D2. For example, the transducer 110 receives the scattered signal in parallel from the signal transduction sections D1 and D2. That is, the transducer 110 receives the scattered signal simultaneously from the signal transduction sections D1, D2. Thus the transducer 110 may receive the scattered signal from the sample volume S1 through the signal transduction section D1, and meanwhile receive the scattered signal from the sample volume S2 through the signal transduction section D2. When the transducer 110 receives the scattered signal in the sample volumes S1 an S2, the scattered signal in the sample volumes S1 and S2 may be transformed into two electric signals, and the signal receiving generator 120 may transmit these electric signals to the signal processor 130.

Next, according to the scattered signal received by the signal transduction sections D1, D2, the maximum Doppler frequencies f1 and f2 are calculated. More specifically, when the signal processor 130 receives these electric signals, the signal processor 130 calculates the maximum Doppler frequency f2 according to the scattered signal received by the signal transduction section D2, and calculate the maximum Doppler frequency f1 according to the scattered signal received by the signal transduction section D1.

In the present embodiment, the signal processor 130 includes a spectrum analyzer 132 and a calculator 134. When the signal processor 130 receives the electric signals from the signal receiving generator 120, the spectrum analyzer 132 analyzes the scattered signal received by the signal transduction sections D1 and D2 to generate a Doppler spectrum graph, as shown in FIG. 2E.

Figure 2E:
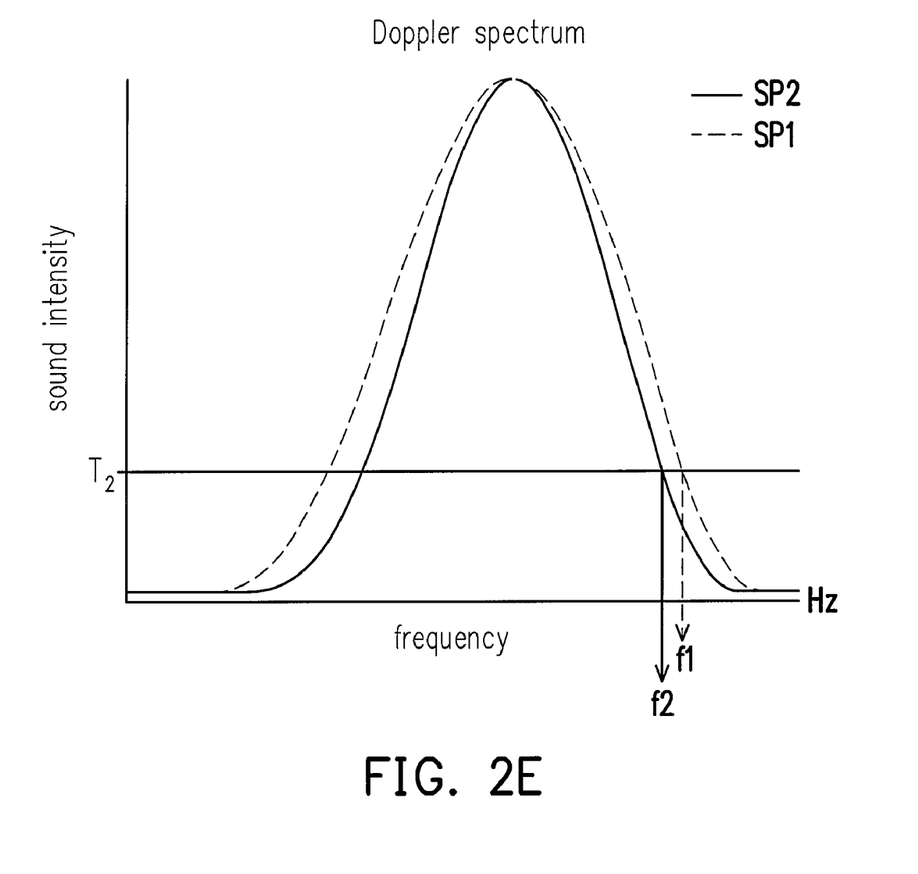
FIG. 2E is a Doppler spectrum graph obtained according to the scattered signal measurement in a plurality of sample volumes in FIG. 2A.

Referring to FIG. 2A, FIG. 2B and FIG. 2E together, the vertical axis in FIG. 2E represents the sound intensity, for example, the absolute intensity (unit is decibel) or relative intensity of sound, and the horizontal axis represents frequency. The spectrum analyzer 132 can generate the Doppler spectrum graph shown in FIG. 2E according to the scattered signal received by the signal transduction sections D1 and D2. In the present embodiment, the spectrum analyzer 132 can perform spectrum analysis on the frequency of the scattered signal received by the signal transduction sections D1 and D2 to generate the Doppler spectrum graph. The spectrum analysis performed by the spectrum analyzer 132 may be Fourier transformation which may be FFT (Fast Fourier transformation) or DFT (Discrete Fourier Transformation). Thus, the spectrum analyzer 132 can plot the spectrum SP1 according to the scattered signal received by the signal transduction section D1, and the spectrum SP2 according to the scattered signal received by the signal transduction section D2.

Of course, the spectrum analyzer 132 may also use methods other than Fourier transformation to generate the Doppler spectrum graph, therefore herein the emphasized the Doppler spectrum graph shown in FIG. 2E is not limited to be obtained using Fourier transformation. Since the width W4 of the sample volume S2 is wider than the width W3 (as shown in FIG. 2A) of the sample volume S1, that is, the time that fluid 202 spent in passing through the sample volume S2 is longer than the time spent in passing through the sample volume S1. Therefore the spectrum SP1 shown in FIG. 2E is wider than the spectrum SP2.

In the present embodiment, a plurality of frequency data of the scattered signal can be obtained from the sample volumes S1, S2 first, for example, the frequency data of 64 to 128 times scattered signal is obtained. Next, the data of these frequencies is subject to Fourier transformation to obtain a plurality of Doppler spectrums. Next, these Doppler spectrums are averaged and normalized to reduce noise, and then more accurate spectrums SP1 and SP2 are further obtained.

After the spectrum analyzer 132 generates the spectrum graph, two maximum Doppler frequencies f1 and f2 are obtained according to the spectrum, wherein the maximum Doppler frequency f1 is obtained according to the scattered signal received by the signal transduction section D1, and the maximum Doppler frequency f2 is obtained according to the scattered signal received by the signal transduction section D2. More specifically, the spectrum analyzer 132 may first set a predetermined threshold T2 (as shown in FIG. 2E) on the vertical axis. The frequency of the spectrum SP1 corresponding to the predetermined threshold T2 is the maximum Doppler frequency f1, while the frequency of the spectrum SP2 corresponding to the predetermined threshold T2 is the maximum Doppler frequency f2, so that the maximum Doppler frequency f1 and the maximum Doppler frequency f2 are obtained.

Next, the flow velocity of fluid 202 is calculated based on these maximum Doppler frequencies f1 and f2. More specifically, after the spectrum analyzer 132 obtains the maximum Doppler frequencies f1 and f2, the data of the maximum Doppler frequencies f1 and f2 are transmitted to the calculator 134. Next, the calculator 134 may calculate the flow velocity of fluid 202 according to the values of the maximum Doppler frequencies f1 and f2.

In the present embodiment, the flow velocity of fluid 202 is calculated by using the following equation (4):

$$V = \sqrt{\left(\lambda \cdot F \frac{f1-f2}{W1-W2}\right)^2 + \left[\frac{\lambda}{2}\left(\frac{W1}{W1-W2}f1 - \frac{W2}{W1-W2}f2\right)\right]^2} \quad (4)$$

Wherein V is the flow velocity of fluid 202, $\lambda$ is the wavelength of the sound wave U, and F is the focal length of the sound wave U. W1 is the width of the signal transduction section D1, and W2 is the width of the signal transduction section D2. $\lambda$, F, W1 and W2 are known parameters, therefore if only the maximum Doppler frequencies f1 and f2 are measured, then V in equation (4) can be calculated. That is, the flow velocity of fluid 202 can be calculated.

The equation (4) may be derived as follows:

$$B_{d1} = 2|f1 - f_{d1}| \quad (5a)$$

$$B_{d2} = 2|f2 - f_{d2}| \quad (5b)$$

$$B_{d1} = \frac{2W1 \cdot V\sin\theta}{\lambda F} \quad (6a)$$

$$B_{d2} = \frac{2W2 \cdot V\sin\theta}{\lambda F} \quad (6b)$$

Wherein $B_{d1}$ is Doppler bandwidth of spectrum SP1, and $B_{d2}$ is Doppler bandwidth of spectrum SP2. The $\theta$ is Doppler angle, i.e. the angle between flow velocity of fluid 202 and the traveling direction of sound wave U. $f_{d1}$ is the frequency to which the maximum intensity value of spectrum SP1 corresponds, while $f_{d2}$ is the frequency to which the maximum intensity value of spectrum SP2 corresponds. That is, $f_{d1}$ is an axial component flow velocity (i.e. $V \cos \theta$) of fluid 202 measured in the sample volume S1, while $f_{d2}$ is an axial component flow velocity of fluid 202 measured in the sample volume S2.

Since the axial component flow velocities of fluid 202 measured in sample volume S1 and S2 are measured under the condition of using the same Doppler angle, that is, $f_{d1}$ and $f_{d2}$ are same or approximate. Therefore, after subtracting equation (5a) with (5b), the equation (7) may be obtained as shown below:

$$f1 - f2 = \frac{1}{2}(B_{d1} - B_{d2}) \quad (7)$$

Next, subtracting equations (6a) and (6b) may yield equation (8), as shown below:

$$B_{d1} - B_{d2} = \frac{2V\sin\theta}{\lambda F}(W1 - W2) \quad (8)$$

The Equation (8) may also be expressed as the following equation (9):

$$V\sin\theta = \frac{\lambda F}{2} \cdot \frac{B_{d1} - B_{d2}}{W1 - W2} \quad (9)$$

Next, after substituting the equation (7) into equation (9), the following equation (10) may be deduced:

$$V \sin\theta = \lambda F \cdot \frac{f1 - f2}{W1 - W2} \tag{10}$$

The lateral component flow velocity $V \sin\theta$ of fluid 202 may be calculated using the equation (10). Next, after substituting the equation (10) into equation (6a), the following equation (11) may be deduced through a simple mathematical calculation:

$$B_{d1} = \frac{2W1 \cdot V\sin\theta}{\lambda F} = \frac{2W1}{\lambda F} \cdot \frac{\lambda F \cdot (f1 - f2)}{W1 - W2} = \frac{2 \cdot W1}{W1 - W2} \cdot (f1 - f2) \tag{11}$$

It can be known from the equation of Doppler shift frequency that the axial component flow velocity $V \cos\theta$ of fluid 202 satisfies the following equation (12), as shown below:

$$V\cos\theta = \frac{\lambda \cdot f_{d1}}{2} \tag{12}$$

By substituting equation (5a) and equation (11) into the equation (12), the following equation (13) may be deduced as shown below:

$$V\cos\theta = \tag{13}$$
$$\frac{\lambda \cdot f_{d1}}{2} = \frac{\lambda}{2} \cdot \left(f1 - \frac{1}{2}B_{d1}\right) = \frac{\lambda}{2} \cdot \left(\frac{W1}{W1 - W2}f2 - \frac{W2}{W1 - W2}f1\right) =$$
$$\frac{\lambda}{2(W1 - W2)} \cdot (W1 \cdot f2 - W2 \cdot f1)$$

Equation (10) and equation (13) may be combined to obtain equation (4) using simple trigonometric function calculation. Therefore, the flow velocity V of fluid 202 can be obtained using the equation (4). In addition, equation (10) and equation (13) may be combined to deduce equation (14) using simple trigonometric function calculation, as shown below:

$$\theta = \tan^{-1}\left[2F \frac{f1 - f2}{W1 \cdot f2 - W2 \cdot f1}\right] \tag{14}$$

It can be known from the equation (14) that the Doppler angle θ can also be calculated using the maximum Doppler frequencies f1 and f2, and then the flow direction of fluid 202 in tube 204 can be obtain or the extending direction of tube 204 can be deduced. For example, the equation (14) of the present embodiment may be applied to measure blood flow direction or deduce the extending direction of blood vessel.

In addition, it can be known from above description, although the flow velocity V of fluid 202 can be obtained directly through calculation according to the maximum Doppler frequencies f1 and f2, however in the present embodiment, the Doppler angle θ may also be calculated first according to equation (14). Then, the flow velocity V of fluid 202 may be calculated according to the calculated Doppler angle θ. More specifically, the Doppler shift frequencies $f_{d1}$ or $f_{d2}$ may be calculated by using the sample volume S1 or S2 first. Next, the Doppler shift frequency equation, i.e. equation (1) may be used by the calculator 134 to calculate the axial component flow velocity $V \cos\theta$ of fluid 202 through the Doppler shift frequencies $f_{d1}$ or $f_{d2}$. Next, after the maximum Doppler frequencies f1 and f2 are measured, the calculator 134 may calculate the Doppler angle θ according to equation (14). Next, using the known axial component flow velocity $V \cos\theta$ of fluid 202 and the Doppler angle θ, the flow velocity V of fluid 202 may be calculated.

It should be noted that the acoustic method for measuring flow velocity of fluid revealed in above FIG. 2A to FIG. 2E employs the transducer 110 having two signal transduction sections D1 and D2 to measure the flow velocity of fluid 202. However, in other embodiments, (without shown in the drawings) the transducer 110 may also have more than two signal transduction sections D1~Dn, wherein n is a positive integer, and n represents the number of the transduction sections. Thus, the transducer 110 can emit a sound wave including a plurality of acoustic beams U1~Un all pointing to the fluid 202 in the tube 204 at the same Doppler angle θ. Next, these signal transduction sections D1~Dn receive the scattered signal scattered from fluid 202 at the same time, and according to the scattered signal received by these signal transduction sections D1~Dn, a plurality of maximum Doppler frequencies f1~fn are obtained, and the flow velocity of fluid 202 is calculated. Of course, the Doppler angle θ may also be calculated from these maximum Doppler frequencies f1~fn. Therefore the transducer 110 and the transducer 110' shown in FIG. 2A to FIG. 2D are only exemplary, which do not limit the present invention as such.

In addition, it should be noted that the acoustic method for measuring flow velocity of fluid of the present embodiment may be applied in medical field, for example, in measuring blood flow velocity, or may be applied in industry. In addition, depending upon the different application fields, sound wave U may be ultrasound or regular sound that can be sensed by human ears.

To sum up, the present invention uses a transducer to measure at least two maximum Doppler frequencies, and further calculates the flow velocity of fluid and Doppler angle. Compared to the prior arts, the present invention can measure flow velocity of fluid and Doppler angle without knowing the Doppler shift frequency. Therefore, the present invention can measure the flow velocity of fluid accurately without being influenced by the shift of the Doppler shift frequency, and obtain the Doppler angle. Moreover, when the maximum Doppler frequencies are known, the equation (4) may be used to calculate the flow velocity of fluid, and the equation (14) may be used to calculate the Doppler angle. Thus, according to an embodiment of the present invention, the flow velocity of the fluid may be precisely calculated by a simple mathematical calculation, and also the Doppler angle may be obtained more accurately.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An acoustic method for measuring flow velocity of fluid, comprising:

transmitting a sound wave to a fluid from a transduction surface of a transducer, wherein the transduction surface comprises at least two signal transduction sections Dn, and wherein n is a positive integer representing number of transducer sections;

receiving a scattered signal from the transduction sections Dn when a sound wave is scattered by the fluid into the scattered signal;

obtaining a plurality of maximum Doppler frequencies fn according to the scattered signal received by the transduction sections Dn; and calculating the flow velocity of the fluid according to the maximum Doppler frequencies fn.

2. The acoustic method for measuring flow velocity of fluid of claim 1, wherein the method of obtaining the maximum Doppler frequencies fn comprises:

analyzing the frequency of the scattered signal received by the signal transduction sections Dn to generate a Doppler spectrum graph; and obtaining the maximum Doppler frequencies fn according to the Doppler spectrum graph.

3. The acoustic method for measuring flow velocity of fluid of claim 2, wherein the method of generating the Doppler spectrum graph comprises performing a spectrum analysis on the frequency of the scattered signal received by the signal transduction sections Dn.

4. The acoustic method for measuring flow velocity of fluid of claim 3, wherein the spectrum analysis comprises Fourier transformation.

5. The acoustic method for measuring flow velocity of fluid of claim 1, wherein the signal transduction sections Dn are a signal transduction section D1 and a signal transduction section D2; and the area of the signal transduction section D2 is smaller than the area of the signal transduction section D1, and the signal transduction section D2 is located inside the signal transduction section D1; and wherein a maximum Doppler frequency f1 is obtained according to the scattered signal received by the signal transduction section D1, and a maximum Doppler frequency f2 is obtained according to the scattered signal received by the signal transduction section D2.

6. The acoustic method for measuring flow velocity of fluid of claim 5, wherein the shapes of the signal transduction section D1 and the signal transduction section D2 are rectangular or circular.

7. The acoustic method for measuring flow velocity of fluid of claim 5, wherein the method of calculating the flow velocity of the fluid comprises:

calculating the flow velocity of the fluid using equation:

$$V = \sqrt{\left(\lambda \cdot F \frac{f1-f2}{W1-W2}\right)^2 + \left[\frac{\lambda}{2}\left(\frac{W1}{W1-W2}f1 - \frac{W2}{W1-W2}f2\right)\right]^2},$$

wherein $\lambda$ is the wavelength of the sound wave, F is the focal length of the sound wave, W1 is the width of the signal transduction section D1, and W2 is the width of the signal transduction section D2.

8. The acoustic method for measuring flow velocity of fluid of claim 5, wherein the method of calculating the flow velocity of the fluid comprises:

calculating a Doppler angle $\theta$ using equation:

$$\theta = \tan^{-1}\left[2F \frac{f1-f2}{W1 \cdot f2 - W2 \cdot f1}\right],$$

wherein F is the focal length of the sound wave, W1 is the width of the signal transduction section D1, and W2 is the width of the signal transduction section D2; and calculating flow velocity of the fluid according to the Doppler angle $\theta$.

* * * * *